United States Patent
Kim et al.

(10) Patent No.: US 7,524,610 B2
(45) Date of Patent: Apr. 28, 2009

(54) OXETANE-CONTAINING COMPOUND, PHOTORESIST COMPOSITION HAVING THE SAME, METHOD OF PREPARING PATTERN USING THE PHOTORESIST COMPOSITION, AND INKJET PRINT HEAD INCLUDING POLYMERIZATION PRODUCTS OF THE OXETANE-CONTAINING COMPOUND

(75) Inventors: Kyu-sik Kim, Yongin-si (KR); Jin-baek Kim, Daejeon-si (KR); Young-ung Ha, Suwon-si (KR); Byung-ha Park, Suwon-si (KR); Ji-young Park, Yongin-si (KR); Su-min Kim, Yongin-si (KR)

(73) Assignee: Samsung Electronics Co., Ltd, Suwon-si (KR)

( * ) Notice: Subject to any disclaimer, the term of this patent is extended or adjusted under 35 U.S.C. 154(b) by 0 days.

(21) Appl. No.: 11/768,632

(22) Filed: Jun. 26, 2007

(65) Prior Publication Data
US 2008/0131787 A1   Jun. 5, 2008

(51) Int. Cl.
G03C 1/73 (2006.01)
G03F 7/004 (2006.01)
G03F 7/20 (2006.01)
G03F 7/30 (2006.01)
C07D 305/00 (2006.01)

(52) U.S. Cl. .......... 430/270.1; 430/9; 430/11; 430/12; 430/14; 430/15; 430/18; 430/325; 430/326; 430/914; 522/31; 522/168; 549/510; 549/511; 347/20; 347/47; 427/466

(58) Field of Classification Search .......... None
See application file for complete search history.

(56) References Cited

U.S. PATENT DOCUMENTS

| 2004/0005735 A1 | 1/2004 | Kang et al. |
| 2005/0112500 A1* | 5/2005 | Nishikubo et al. ....... 430/281.1 |
| 2006/0127813 A1* | 6/2006 | Ohkuma et al. ............ 430/311 |
| 2006/0262157 A1 | 11/2006 | Park et al. |

FOREIGN PATENT DOCUMENTS

| JP | 2006-159762 | 6/2006 |
| KR | 2003-0051419 | 6/2003 |
| KR | 2004-37858 | 5/2004 |
| KR | 2006-68915 | 6/2006 |
| WO | WO 01/73510 | 10/2001 |

OTHER PUBLICATIONS

Korean Office Action dated Oct. 26, 2007 issued in KR 2006-0120080.
European Search Report dated Apr. 11, 2008 issued in EP 07111334.4.
E.J.K. Verstegen, J.G. Kloosterboer, J. Lub; Philips Research Laboratories, Department of Polymers & Organic Chemistry, Professor Holstlaan 4, 4545 AA Eindhoven, The Neverlands; XP-002473914; (Synthesis and Photopolymerization of Oxetanes Derived from Bisphenol A).

* cited by examiner

*Primary Examiner*—Sin J. Lee
(74) *Attorney, Agent, or Firm*—Stanzione & Kim, LLP

(57) ABSTRACT

An oxetane-containing compound, a photoresist composition including the same, a method of preparing patterns using the photoresist composition, and an inkjet print head including polymerization products of the oxetane-containing compound.

20 Claims, 6 Drawing Sheets

OXETANE-CONTAINING COMPOUND, PHOTORESIST COMPOSITION HAVING THE SAME, METHOD OF PREPARING PATTERN USING THE PHOTORESIST COMPOSITION, AND INKJET PRINT HEAD INCLUDING POLYMERIZATION PRODUCTS OF THE OXETANE-CONTAINING COMPOUND

CROSS-REFERENCE TO RELATED APPLICATIONS

This application claims priority under 35 U.S.C. §119(a) from Korean Patent Application No. 10-2006-0120080, filed on Nov. 30, 2006, in the Korean Intellectual Property Office, the disclosure of which is incorporated herein in its entirety by reference.

BACKGROUND OF THE INVENTION

1. Field of the Invention

The present general inventive concept relates to an oxetane-containing compound, a photoresist composition including the same, a method of preparing patterns using the photoresist composition, and an inkjet print head including polymerization products of the oxetane-containing compound.

2. Description of the Related Art

Photoresists are used in photolithography to form various patterns. A photoresist is a photosensitive resin that is used to obtain images corresponding to exposed patterns depending on changes of solubility of a developing solution due to light exposure. The photoresist can be classified into two types: a positive photoresist and a negative photoresist. In the positive photoresist, a desired pattern is obtained by removing exposed regions during developing since the solubility of the exposed regions of the developing solution increases. In the negative photoresist, a desired pattern is obtained by removing unexposed regions during developing since the solubility of the exposed regions of the developing solution decreases.

The photoresist is mixed with a solvent, etc., and the mixture can be coated on a substrate to prepare a structure having a specific pattern through exposing and developing. For example, a method of preparing a pattern using polycarbomethylsilane derivative as a photoresist is disclosed in Korean Patent Publication No. 2004-0037858.

Pattern formation technology using a photoresist can be widely applied in many technological fields, for example, in inkjet print head and micro electro mechanical systems (MEMS) switch manufacturing.

Inkjet printers are devices to print an image on a printing medium by ejecting droplets of ink from inkjet print heads onto a desired region of the printing medium. Inkjet print heads can be classified into two types depending on the mechanism to eject ink droplets: thermal inkjet print heads and piezoelectric inkjet print heads. Thermal inkjet print heads generate bubbles in the ink by using heat and eject the ink utilizing an expansion force of the bubbles, and the piezoelectric inkjet print heads eject ink using pressure generated by deforming a piezoelectric material. Inkjet print heads include a chamber layer and/or a nozzle layer having suitable patterns to eject ink and that are attached to a substrate to support the chamber layer and the nozzle layer. Further, thermal inkjet print heads need excellent thermal resistance in the chamber layer and/or the nozzle layer.

Meanwhile, MEMS switches are a type of radio frequency (RF) devices that are widely manufactured using MEMS technologies, and various sacrificial layers are needed to manufacture MEMS switches.

Accordingly, there is a need to develop a photoresist composition that is suitable for a variety of devices, such as inkjet print heads or MEMS switches.

SUMMARY OF THE INVENTION

The present general inventive concept provides an oxetane-containing compound which provides polymerization products formed of the compound with excellent thermal resistance, chemical resistance, adhesion property, and the like. The present general inventive concept also provides a photoresist composition using the oxetane-containing compound, a method of preparing patterns using the photoresist composition, and an inkjet print head including polymerization products of the oxetane-containing compound.

Additional aspects and utilities of the present general inventive concept will be set forth in part in the description which follows and, in part, will be obvious from the description, or may be learned by practice of the general inventive concept.

The foregoing and/or other aspects and utilities of the present general inventive concept may be achieved by providing an oxetane-containing compound represented by at least one of Formula 1, Formula 2, and a mixture thereof:

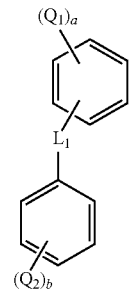

Formula 1

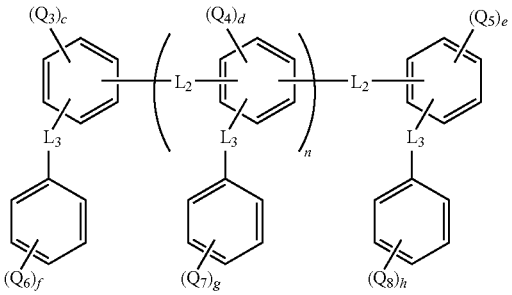

Formula 2

Here, $Q_1$, $Q_2$, $Q_3$, $Q_4$, $Q_5$, $Q_6$, $Q_7$, and $Q_8$ can each independently be a hydrogen atom, a hydroxyl group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_4$-$C_{30}$ aliphatic hydrocarbon ring, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ acyl group, or a substituted or unsubstituted ether bond-containing monovalent group, $Q_1$, $Q_2$, $Q_3$, $Q_4$, $Q_5$, $Q_6$, $Q_7$, and $Q_8$ are identical to or different from each other, at least one of the hydrogen atoms in at least one of $Q_1$ and $Q_2$, and at least one of the hydrogen atoms in at least one of $Q_3$, $Q_4$, $Q_5$, $Q_6$, $Q_7$, and $Q_8$ can be substituted with an oxetane group, a can be 1, 2, 3, or 4, b can be 1, 2, 3, 4, or 5, c and e can each independently be 1, 2 or 3; d can be 1 or 2; f, g, and h can each independently be 1, 2, 3, or 4, $L_1$, $L_2$, and $L_3$ can each independently be a substituted or unsubstituted $C_1$-$C_{30}$ alkylene group, a substituted or unsubstituted $C_2$-$C_{30}$ alkenylene group, a substituted or unsubstituted $C_2$-$C_{30}$ alkynylene group, a substituted or unsubstituted $C_6$-$C_{30}$ arylene group, a substituted or unsubstituted $C_3$-$C_{30}$ heteroarylene group, or a substituted or unsubstituted ether bond-containing divalent group, and n can be 0 or an integer 1-10.

The foregoing and/or other aspects and utilities of the present general inventive concept may also be achieved by providing a photoresist composition including an oxetane-containing compound, a photo initiator, and a solvent.

The foregoing and/or other aspects and utilities of the present general inventive concept may also be achieved by providing a method of forming a pattern, the method including coating a photoresist composition having an oxetane-containing compound on a substrate, and exposing the coated photoresist composition to light according to a specific pattern and developing the resultant to obtain a structure having the pattern.

The foregoing and/or other aspects and utilities of the present general inventive concept may also be achieved by providing a substrate through which an ink feed hole to supply ink is formed, a chamber layer including a plurality of ink chambers filled with ink supplied from the ink feed hole, and a nozzle layer comprising a plurality of nozzles through which the ink is ejected, wherein at least one of the chamber layer and the nozzle layer includes polymerization products of an oxetane-containing compound.

The foregoing and/or other aspects and utilities of the present general inventive concept may also be achieved by providing a compound usable as a photoresist composition, including at least one oxetane ring.

BRIEF DESCRIPTION OF THE DRAWINGS

These and/or other aspects and utilities of the present general inventive concept will become apparent and more readily appreciated from the following description of the embodiments, taken in conjunction with the accompanying drawings of which.

DETAILED DESCRIPTION OF THE PREFERRED EMBODIMENTS

Figure 1:
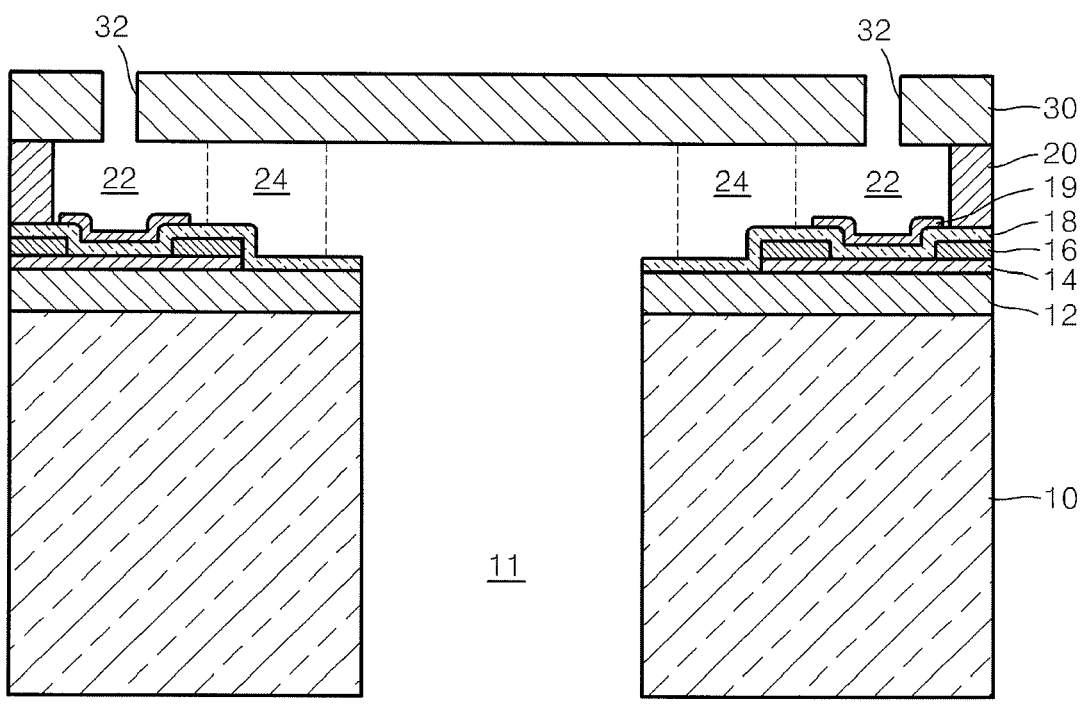
FIG. 1 is cross-sectional view illustrating an inkjet print head according to an embodiment of the present general inventive concept.

Reference will now be made in detail to the embodiments of the present general inventive concept, examples of which are illustrated in the accompanying drawings, wherein like reference numerals refer to the like elements throughout. The embodiments are described below in order to explain the present general inventive concept by referring to the figures.

An oxetane-containing compound according to an embodiment of the present general inventive concept may include at least one oxetane ring. An oxetane ring is a 4-membered ring having three carbon atoms and one oxygen atom, and thus, a compound including the oxetane ring can have an excellent polymerizability. For example, an oxetane-containing compound may be polymerized to form a polymer with a molecular weight of about 5 times greater than a molecular weight of a polymer polymerized by an epoxy resin including an oxirane ring under same polymerization conditions.

The oxetane-containing compound according to an embodiment of the present general inventive concept may be represented by a formula similar to that of Formula 1 or Formula 2 below.

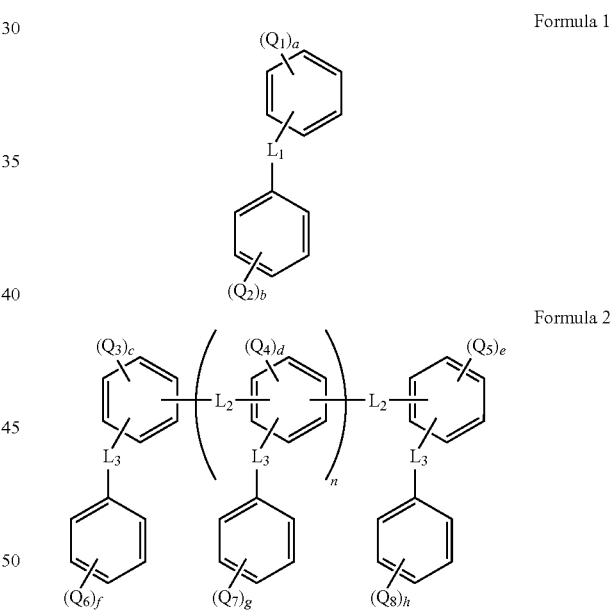

Formula 1

Formula 2

Here, $Q_1$, $Q_2$, $Q_3$, $Q_4$, $Q_5$, $Q_6$, $Q_7$, and $Q_8$ can each independently be a hydrogen atom, a hydroxyl group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_4$-$C_{30}$ aliphatic hydrocarbon ring, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ acyl group, or a substituted or unsubstituted ether bond-containing monovalent group.

Meanwhile, at least one of the hydrogen atoms in $Q_1$, and $Q_2$, and at least one of the hydrogen atoms in $Q_3$, $Q_4$, $Q_5$, $Q_6$, $Q_7$, and $Q_8$ may be substituted with an oxetane group. Preferably, the oxetane group may be represented by a formula similar to Formula 3.

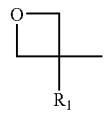

Formula 3

Here, $R_1$ can be a hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid or a salt thereof, a carbonyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_6$-$C_{30}$ aryl group, or a substituted or unsubstituted $C_2$-$C_{30}$ heteroaryl group.

Preferably, $R_1$ can be a hydrogen atom or a substituted or unsubstituted $C_1$-$C_{10}$ alkyl group.

Accordingly, the oxetane-containing compound according to an embodiment of the present general inventive concept may include at least one oxetane group.

Examples of the unsubstituted $C_1$-$C_{30}$ alkyl group may include a methyl group, an ethyl group, a propyl group, an iso-butyl group, a sec-butyl group, a pentyl group, an iso-amyl group, and a hexyl group. At least one of the hydrogen atoms in the alkyl group may be substituted with an oxetane group (for example, an oxetane represented by Formula 3), a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid or a salt thereof, a carbonyl group, a $C_1$-$C_{30}$ alkyl group, a $C_2$-$C_{30}$ alkenyl group, a $C_2$-$C_{30}$ alkynyl group, a $C_6$-$C_{30}$ aryl group, a $C_7$-$C_{20}$ arylalkyl group, a $C_2$-$C_{30}$ heteroaryl group, a $C_3$-$C_{30}$ heteroarylalkyl group, a $C_6$-$C_{30}$ aryloxy group, or —N($Z_1$)($Z_2$).

$Z_1$ and $Z_2$ can each independently be a hydrogen atom, a substituted or unsubstituted $C_1$-$C_{30}$ alkyl group, a substituted or unsubstituted $C_1$-$C_{30}$ haloalkyl group, a substituted or unsubstituted $C_6$-$C_{30}$ aryl group, a substituted or unsubstituted $C_6$-$C_{30}$ haloaryl group or a substituted or unsubstituted $C_2$-$C_{30}$ heteroaryl group.

The unsubstituted $C_2$-$C_{30}$ alkenyl group is a group having a carbon-carbon double bond in the center or at one end of the alkyl group. The unsubstituted $C_2$-$C_{30}$ alkenyl group may be ethylene, propylene, butylene, hexylene, or the like. At least one of the hydrogen atoms in the alkenyl group may be substituted with the substituent described in the alkyl group.

The unsubstituted $C_2$-$C_{30}$ alkynyl group is a group having a carbon-carbon triple bond in the center or at one end of the alkyl group. The unsubstituted $C_2$-$C_{30}$ alkynyl group may be acetylene, propylene, phenylacetylene, naphthylacetylene, iso-propylacetylene, t-butylacetylene, diphenylacetylene, or the like. At least one of the hydrogen atoms in the alkynyl group may be substituted with the substituent described in the alkyl group.

The unsubstituted $C_1$-$C_{30}$ alkoxy group can be represented by —$OA_1$, wherein, $A_1$ is the alkyl group. Examples of the alkoxy group may include methoxy, ethoxy, phenyloxy, cyclohexyloxy, naphthyloxy, isopropyloxy, and diphenyloxy, and at least one hydrogen atom in the alkoxy group may be substituted with the substituent described in the alkyl group.

Examples of the unsubstituted $C_4$-$C_{30}$ aliphatic hydrocarbon ring may include a cyclohexyl group, and a cycloheptyl group, but are not limited thereto, and at least one hydrogen atom in the aliphatic hydrocarbon ring may be substituted with the substituent described in the alkyl group. Further, a carbon in the aliphatic hydrocarbon ring may be substituted with

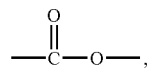

etc., resulting in structural deformation of the aliphatic hydrocarbon ring, for example to form a cyclic ester, such as lactone.

The unsubstituted $C_6$-$C_{30}$ aryl group is a carboncyclic aromatic system having 6-30 carbon atoms and at least one aromatic ring, wherein at least one of the rings may be fused with each other or bonded by a single bond. At least one of the hydrogen atoms in the aryl group may be substituted with the substituent described in the alkyl group.

Examples of the substituted or unsubstituted $C_6$-$C_{30}$ aryl group may include a phenyl group, a $C_1$-$C_{10}$alkylphenyl group (e.g., an ethylphenyl group), a halophenyl group (e.g., an o-, m- and p-fluorophenyl group and a dichlorophenyl group), a cyanophenyl group, a dicyanophenyl group, a trifluoromethoxyphenyl group, a biphenyl group, a halobiphenyl group, a cyanobiphenyl group, a $C_1$-$C_{10}$ biphenyl group, a $C_1$-$C_{10}$ alkoxybiphenyl group, an o-, m-, and p-tolyl group, an o-, m- and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), a cyanonaphthyl group, an acthracenyl group, a azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a pyranthrenyl group, and an ovalenyl group.

The unsubstituted $C_2$-$C_{30}$ heteroaryl group is an aromatic ring system including carbon rings and at least one hetero atom, such as nitrogen, oxygen, phosphor, and sulfur, wherein at least one aromatic ring may be fused with each other or bonded by a single bond. At least one of the hydrogen atoms in the heteroaryl group may be substituted with the substituent described in the alkyl group.

Examples of the unsubstituted $C_2$-$C_{30}$ heteroaryl group may include a pyrazolyl group, an imidazolyl group, an oxazolyl group, a thiozolyl group, a triazolyl group, a tetrazolyl group, an oxadiazolyl group, a pyridinyl group, a pyridazinyl group, a pyrimidinyl group, a triazynyl group, a carbazolyl group, an indolyl group, a quinolinyl group, and an isoquinolinyl group.

The unsubstituted $C_6$-$C_{30}$ aryloxy group can be a group represented by —$OA_2$, wherein the $A_2$ is an aryl group, such as a phenoxy group. At least one of the hydrogen atoms in the aryloxy group may be substituted with the substituent described in the alkyl group.

The unsubstituted $C_6$-$C_{30}$ acyl group can be a group represented by —$COA_3$, wherein the $A_3$ is an alkyl group or an aryl group, such as an acetyl group (—$COCH_3$) and a benzoyl group (—$COC_6H_5$). At least one of the hydrogen atoms in the acyl group may be substituted with the substituent described in the alkyl group.

The unsubstituted ether bond-containing monovalent group can be an alkyl group, alkenyl group, alkynyl group, or alkoxy group in which at least one of the carbon atoms is substituted with a —C—O— bond. At least one of the hydrogen atoms in the ether bond-containing monovalent group may be substituted with the substituent described in the alkyl group.

Preferably, $Q_1$, $Q_2$, $Q_3$, $Q_4$, $Q_5$, $Q_6$, $Q_7$, and $Q_8$ may each independently be a hydrogen atom, a hydroxyl group, a $C_1$-$C_{30}$ alkoxy group substituted with an oxetane group or a carbonyl group, a $C_1$-$C_{30}$ alkyl group substituted with an oxetane group or a carbonyl group, or an ether bond-containing monovalent group substituted with an oxetane group or a hydroxyl group. $Q_1$, $Q_2$, $Q_3$, $Q_4$, $Q_5$, $Q_6$, $Q_7$, and $Q_8$ may also each independently be a hydrogen atom, a hydroxyl group, a $C_1$-$C_{10}$ alkoxy group substituted with an oxetane group or a carbonyl group, a $C_1$-$C_{10}$ alkyl group substituted with an oxetane group or a carbonyl group, or an ether bond-containing monovalent group substituted with an oxetane group or a hydroxyl group. At least one of the hydrogen atoms in $Q_1$ and $Q_2$, and at least one of the hydrogen atoms in the $Q_3$, $Q_4$, $Q_5$, $Q_6$, $Q_7$, and $Q_8$ may be substituted with the oxetane group, and the oxetane group may be an oxetane group represented by a formula similar to Formula 3.

Furthermore, $Q_1$, $Q_2$, $Q_3$, $Q_4$, $Q_5$, $Q_6$, $Q_7$, and $Q_8$ may each independently be a hydrogen atom or one structure similar to those represented by Formula 4.

Formula 4

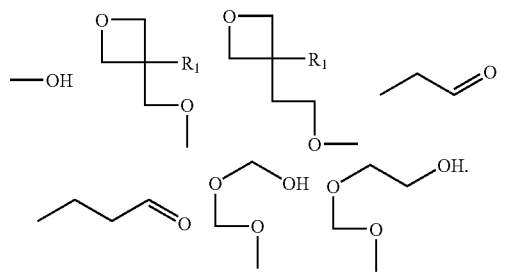

In Formula 1 or 2, a, b, c, d, e, f, g, and h indicate that there may be a plurality of $Q_1$, $Q_2$, $Q_3$, $Q_4$, $Q_5$, $Q_6$, $Q_7$, and $Q_8$. $Q_1$, $Q_2$, $Q_3$, $Q_4$, $Q_5$, $Q_6$, $Q_7$, and $Q_8$ may be identical to or different from each other. For example, when a is 2, there may be two $Q_1$, wherein the $Q_1$s may be identical to or different from each other.

In Formulae 1 and 2, a can be 1, 2, 3, or 4, b can be 1, 2, 3, 4, or 5, c and e can each independently be 1, 2, or 3, d can be 1 or 2, and f, g, and h can each independently be 1, 2, 3, or 4.

In Formulae 1 and 2, $L_1$, $L_2$, and $L_3$ may each independently be a substituted or unsubstituted $C_1$-$C_{30}$ alkylene group, a substituted or unsubstituted $C_2$-$C_{30}$ alkenylene group, a substituted or unsubstituted $C_2$-$C_{30}$ alkynylene group, a substituted or unsubstituted $C_6$-$C_{30}$ arylene group, a substituted or unsubstituted $C_3$-$C_{30}$ heteroarylene group, or a substituted or unsubstituted ether bond-containing divalent group.

The unsubstituted $C_1$-$C_{30}$ alkylene group can be a divalent linking group having a structure similar to the alkyl group, and examples of the unsubstituted $C_1$-$C_{30}$ alkylene group may be a methylene group and an ethylene group. At least one of the hydrogen atoms in the alkylene group may be substituted with the substituent described in the alkyl group.

Meanwhile, the unsubstituted $C_2$-$C_{30}$ alkenylene group, the unsubstituted $C_2$-$C_{30}$ alkynylene group, the unsubstituted $C_6$-$C_{30}$ arylene group, the unsubstituted $C_3$-$C_{30}$ heteroarylene group, the unsubstituted ether bond-containing divalent group can be divalent linking groups having structures similar to the alkenyl group, the alkynyl group, the aryl group, the heteroaryl group, and the ether bond-containing monovalent group, respectively. At least one of the hydrogen atoms in the groups may be substituted with the substituent described in the alkyl group.

Preferably, $L_1$, $L_2$, and $L_3$ may each independently be at least one structure similar to the structures represented by Formula 5.

Formula 5

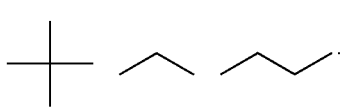

In Formula 2, n may be 0 or an integer 1-10, and preferably 0 or an integer 1-5.

For example, the oxetane-containing compound according to an embodiment of the present general inventive concept may be represented by Formula 6 or 7 below, but is the present general inventive concept is not limited thereto.

Formula 6

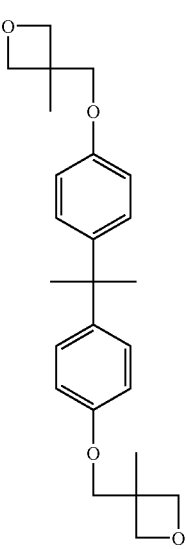

Formula 7

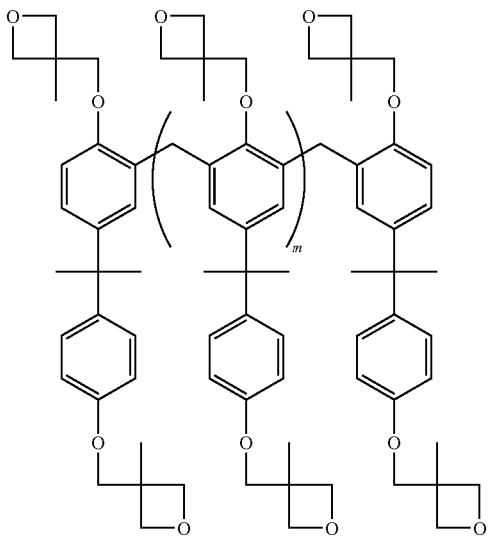

In Formula 7, m can be 0, 1, or 2.

The compound represented by Formula 6 includes two oxetane groups. However, at least one methoxy group substituted with the oxetane group may be another substituent, such as a hydroxyl group depending on synthesis conditions. Similarly, the compound represented by Formula 7 may include 4-8 oxetane groups depending on m. However, at least one methoxy group substituted with the oxetane group may be another substituent, such as a hydroxyl group, depending on synthesis conditions. Such process may be easily understood by one of ordinary skill in the art based on the synthesis of the oxetane-containing compound according to an embodiment of the present general inventive concept, which will be described later.

The oxetane-containing compound represented by Formula 1 or 2 may be synthesized using various methods. For example, the oxetane-containing compound represented by Formula 1 or 2 may be synthesized by reacting an oxetane-containing sulfonic acid ester or an oxetane-containing halogenated alkane with a benzene ring-containing compound.

The oxetane-containing sulfonic acid ester may be synthesized by reacting an oxetane-containing alcohol with a halide including a —(O=S=O)— bond. Meanwhile, the oxetane-containing halogenated alkane may be synthesized by halogenating an oxetane-containing alcohol or the oxetane-containing sulfonic acid ester, for example using $CBr_4$, NaBr, or the like. After the oxetane-containing compound synthesis is terminated, the oxetane-containing sulfonic acid ester remains in a solid state, and the oxetane-containing halogenated alkane remains in a liquid state. Thus, a possibility of the oxetane-containing halogenated alkane acting as an impurity in the synthesized oxetane-containing compound is less than a possibility of the oxetane-containing sulfonic acid ester acting as an impurity in the synthesized oxetane-containing compound. The oxetane-containing sulfonic acid ester may be toluene-4-sulfonic acid 3-methyl-oxetane-3-yl methyl ester, and the oxetane-containing halogenated alkane may be 3-methyl-3-(bromomethyl)oxetane, but they are not limited thereto.

In the synthesis, since the oxetane-containing sulfonic acid ester or the oxetane-containing halogenated alkane is not reacted 100% with the benzene ring-containing compound, the oxetane-containing compound according to an embodiment of the present general inventive concept may include other groups in addition to the oxetane group as described in Formula 1 or 2.

The benzene ring-containing compound may be any benzene ring-containing compound that is commonly used to synthesize the oxetane-containing compound represented by Formula 1 or 2. For example, a novolak resin which is commercially available may be used. More particularly, the novolak resin may be bisphenol A, but the present general inventive concept is not limited thereto.

Polymerization of the oxetane-containing compound represented by Formula 1 or 2 may be initiated by being exposed to light, and thus the oxetane-containing compound may be used as a photoresist of a photoresist composition according to an embodiment of the present general inventive concept. Accordingly, the photoresist composition of the present embodiment of the general inventive concept may include the oxetane-containing compound represented by Formula 1 or 2, a photo initiator, and a solvent. The oxetane-containing compound is described above.

The photo initiator initiates the polymerization of the oxetane-containing compound when the photoresist composition is exposed to light.

The photo initiator may be an onium salt of a Group 15 element, an onium salt of a Group 16 element, such as a sulfonium salt, an aromatic halonium salt, such as an aromatic iodonium salt, or a mixture thereof, but the present general inventive concept is not limited thereto.

Examples of the sulfonium salt may include triphenylsulfonium tetrafluoroborate, methyldiphenylsulfonium tetrafluoroborate, dimethyldiphenylsulfonium hexafluorophosphate, triphenylsulfonium hexafluorophosphate, triphenylsulfonium hexafluoroantimonate, dipenylnaphthylsulfonium hexafluoroarsenate, tritolysulfonium hexafluorophosphate, anisyldiphenylsulfonium hexafluoroantimonate, 4-butoxyphenyldiphenylsulfonium tetrafluoroborate, 4-chlorophenyldiphenylsulfonium hexafluoroantimonate, tris(4-phenoxyphenyl)sulfonium hexafluorophosphate, di(4-ethoxyphenyl)methylsulfonium hexafluoroarsenate, 4-acetoxyphenyldiphenylsulfonium tetrafluoroborate, tris(4-thiomethoxyphenyl)sulfonium hexafluorophosphate, di(methoxysulfophenyl)methylsulfonium hexafluoroantimonate, di(methoxynaphthyl)methylsulfonium tetrafluoroborate, di(carbomethoxyphenyl)methylsulfonium hexafluorophosphate, 4-aceteamidophenyldiphenylsulfonium tetrafluoroborate, dimethylnaphthyl sulfonium hexafluorophosphate, trifluoromethyldiphenylsulfonium tetrafluoroborate, methyl(n-methylphenothiazinyl)sulfonium hexafluoroantimonate, phenylmethylbenzylsulfonium hexafluorophosphate and derivatives thereof, but the present general inventive concept is not limited thereto.

Further, examples of the aromatic iodonium salt may include diphenyliodonium tetrafluoroborate, di(4-methylphenyl)iodonium tetrafluoroborate, phenyl-4-methylphenyliodonium tetrafluoroborate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, diphenyliodonium hexafluorophosphate, di(4-methylphenyl)iodonium hexafluorophosphate, diphenyliodonium hexafluoroarsenate, di(4-phenoxyphenyl)iodonium tetrafluoroborate, phenyl-2-thienyliodonium hexafluorophosphate, 3,5-dimethylpyrazolyl-4-phenyliodonium hexafluorophosphate, diphenyliodonium hexafluoroantimonate, 2,2'-diphenyliodonium tetrafluoroborate, di(2,4-dichlorophenyl) iodonium hexafluorophosphate, di(4-bromophenyl)

iodonium hexafluorophosphate, di(4-methoxyphenyl) iodonium hexafluorophosphate, di(3-carboxyphenyl) iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzoethienyl)iodonium hexafluorophosphate and derivatives thereof, but is not limited thereto.

The amount of the photo initiator may be in the range of about 5-20 parts by weight, and preferably of about 8-16 parts by weight based on 100 parts by weight of the oxetane-containing compound. When the amount of the photo initiator is less than 5 parts by weight based on 100 parts by weight of the oxetane-containing compound, the polymerization of the oxetane-containing compound may not be effectively performed when exposed to light. On the other hand, when the amount of the photo initiator is greater than 20 parts by weight based on 100 parts by weight of the oxetane-containing compound, a Line-Width variation in which a size of the pattern becomes greater than the real size of a mask due to acid diffusion and a T-top and Foot phenomenon in which the pattern is deformed due to neutralization of the acid may occur.

Meanwhile, examples of the solvent may include γ-butyrolactone, cyclopentanone, $C_1$-$C_6$ acetate, tetrahydrofuran, xylene, and a mixture thereof, but the present general inventive concept is not limited thereto.

The amount of the solvent may be in the range of about 30-100 parts by weight, and preferably of about 30-80 parts by weight based on 100 parts by weight of the oxetane-containing compound. When the amount of the solvent is less than 30 parts by weight based on 100 parts by weight of the oxetane-containing compound, printability of the photoresist composition may decrease. On the other hand, when the amount of the solvent is greater than 100 parts by weight based on 100 parts by weight of the oxetane-containing compound, the viscosity of the photoresist composition may decrease due to relatively low amount of solid content, and thus the thickness of layers may not be controlled during coating.

The photoresist composition may further include silane coupling agents, dyestuffs, surfactants, and the like in addition to the oxetane-containing compound, the photo initiator, and the solvent. A filler, such as barium sulfate, talc, and glass bubble, and a viscosity modifier, such as silica, may further be included in the photoresist composition, and any additive that is used to improve properties of the photoresist composition may be also included therein. Such additives may be easily selected by one of ordinary skill in the art.

The photoresist composition may be used to form various patterns. More particularly, a method of preparing patterns using the photoresist composition may include coating a photoresist composition on a substrate, and exposing the coated photoresist composition to light according to a specific pattern and developing the resultant to obtain a structure having the pattern.

The photoresist composition may be coated using a printing method that is commonly used in the art, for example, spin coating, dipping, inkjet printing, or the like.

In the exposing the coated photoresist composition to light, a photo mask may be used depending on a desired pattern to be formed. The coated photoresist composition may be selectively heat treated before and/or after being exposed to light. When the photoresist composition is heat treated before being exposed to light, the solvent is removed, and thus a flat layer may be formed. Further, when the photoresist composition is heat treated after being exposed to light, Tg of a polymer in the coating layer increases, and thus an acid that is generated due to light is effectively diffused to below the substrate. Further, a crosslinking polymerization may be accelerated by the heat treatment.

When the coated photoresist composition is exposed to light, the polymerization of the oxetane-containing compound is initiated by the photo initiator in the exposed region of the photoresist composition to form a polymer which is not dissolved in a developing solution. Thus, a structure including the polymerization products of the oxetane-containing compound according to an embodiment of the present general inventive concept and the pattern corresponding to the exposed region may be obtained. The developing solution may be propylene glycol monomethyl ether acetate (PG-MEA), ethylacetate, diacetone alcohol, or the like, but the present general inventive concept is not limited thereto.

The structure may be an insulating layer having a specific pattern. For example, the structure may comprise a chamber layer and/or a nozzle layer of an inkjet print head. An inkjet print head according to an embodiment of the present general inventive concept may include a substrate through which an ink feed hole to supply ink is installed, a chamber layer including a plurality of ink chambers filled with ink supplied from the ink feed hole, and a nozzle layer including a plurality of nozzles through which the ink is ejected. More particularly, a thermal inkjet print head according to an embodiment of the present general inventive concept is illustrated in FIG. 1.

The inkjet head illustrated in FIG. 1 includes a substrate 10, a chamber layer 20 on the substrate 10, and a nozzle layer 30 on the chamber layer 20. A plurality of ink chambers 22 in which ink to be ejected is filled are formed in the chamber layer 20, and nozzles 32 through which the ink is ejected are formed in the nozzle layer 30. The chamber layer 20 and the nozzle layer 30 are formed by using the photoresist composition including the oxetane-containing compound according to an embodiment of the present general inventive concept. Thus, the chamber layer 20 and the nozzle layer 30 may include polymerization products of the oxetane-containing compound according to an embodiment of the present general inventive concept.

An ink feed hole 11 through which the ink is supplied to the ink chambers 22 is formed through the substrate 10. Further, a plurality of restrictors 24 connecting the ink chambers 22 and the ink feed hole 11 are formed in the chamber layer 20. In general, the substrate 10 may be a silicon substrate. An insulating layer 12 is formed on the substrate 10 to insulate heaters 14 from the substrate 10. The heaters 14 are formed on the insulating layer 12 to form bubbles by heating the ink in the ink chambers 22, and electrodes 16 are formed on the heaters 14 to apply current to the heaters 14. A passivation layer 18 can be formed on the surface of the heaters 14 and the electrodes 16 to protect them, and an anti-cavitation layer 19 can be formed on the passivation layer 18 to protect the heaters 14 from cavitation force which occurs when the bubbles are removed.

The chamber layer 20 and the nozzle layer 30 are formed by using the photoresist composition including the oxetane-containing compound according to an embodiment of the present general inventive concept, and thus include the polymerization products of the oxetane-containing compound according to an embodiment of the present general inventive concept. Therefore, the chamber layer 20 and the nozzle layer 30 do not deform at a high temperature since they have excellent thermal resistance, and thus they also have excellent durability. Further, a cost of manufacturing the inkjet print head may decrease since the oxetane-containing compound according to an embodiment of the present general inventive concept is a cost-effective compound.

Meanwhile, the structure may be a sacrificial layer to expose a metal layer to form a MEMS switch. The MEMS switch is described in more detail in Korean Patent Publication No. 2006-0068915, the disclosure of which is incorporated herein in its entirety by reference.

The present general inventive concept will now be described in detail with reference to the following examples:

SYNTHESIS EXAMPLE 1

Synthesis of toluene-4-sulfonic acid-3-methyl-oxetane-3-yl methyl ester

Toluene-4-sulfonic acid 3-methyl-oxetane-3-yl methyl ester was synthesized through Reaction Scheme 1 as follows.

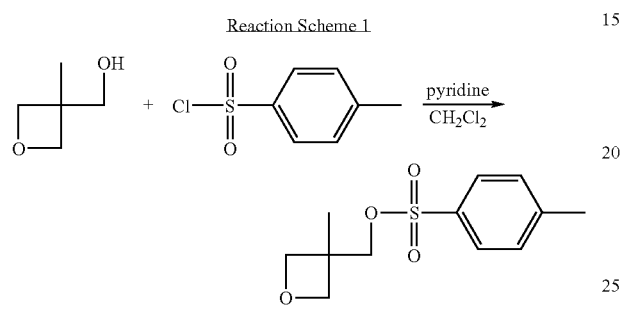

Reaction Scheme 1

57.20 g (0.3 mmol) of p-toluene sulfonyl chloride was added to 250 ml of pyridine under nitrogen atmosphere mixture, and the mixture was cooled in ice water. When the mixture was cooled, 20 ml (MOMT: 20.68 g, 0.20 mmol) of 3-methyl-3-oxetane-methanol) was gradually added thereto and the mixture was reacted for 2 hours. After the reaction terminated, the resultant mixture was added to 2 L of ice water (1:1, v/v) and stirred for 30 minutes. The obtained precipitate was filtered, washed with water, and dried in a vacuum to obtain toluene-4-sulfonic acid 3-methyl-oxetane-3-yl methyl ester (Yield: 90%). NMR spectroscopy of the resulting product was:

$^{1}$H NMR (CDCl$_{3}$, 300 MHz): δ 7.78 (d, 2H), 7.34(d, 2H), 4.31(m, 4H), 4.04(s, 2H), 2.43(s, 3H), 1.27(s, 3H)

SYNTHESIS EXAMPLE 2

Synthesis of an oxetane-containing Compound (I)

An oxetane-containing compound was synthesized through Reaction Scheme 2 as follows.

Reaction Scheme 2

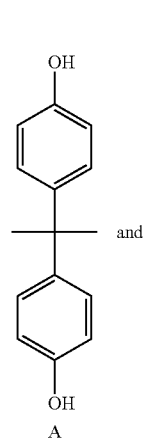
and

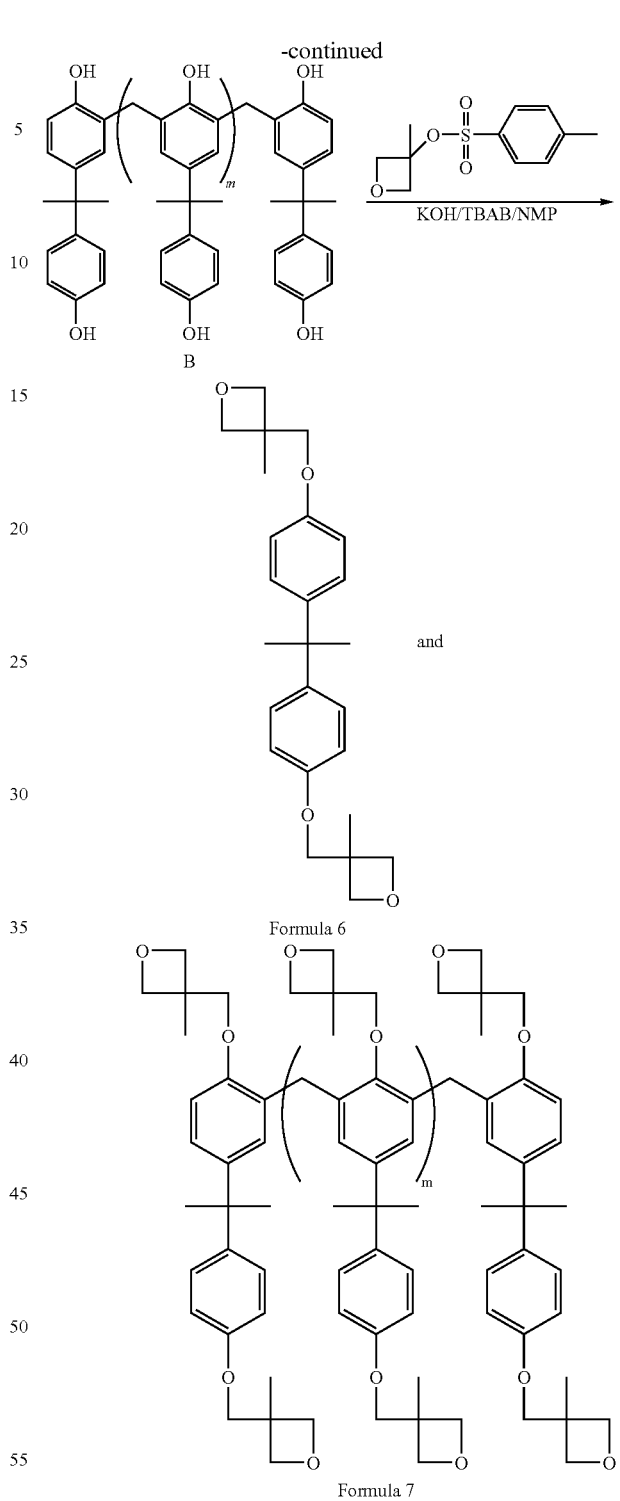

Formula 6

Formula 7

5 g (5.0 mol) of novolak resin illustrated in Reaction Scheme 2 (a mixture of compound A and compound B illustrated in Reaction Scheme 2, where m is 0, 1 or 2) and 5.6 g (0.1 mol) of KOH were dissolved in 20 ml of N-methyl-2-pyrrolidone (NMP) at room temperature. 15.38 g (0.06 mol) of toluene-4-sulfonic acid 3-methyl-oxetane-3-yl methyl ester obtained according to Synthesis Example 1 and 0.6 g (0.002 mol) of tetrabutylammonium bromide were added thereto. The mixture was reacted at 70° C. for 48 hours, and placed in water. The obtained precipitate was filtered under reduced pressure, washed several times with a KOH solution and water, and dried in a vacuum to obtain 5.3 g of a mixture of a compound represented by Formula 6 and a compound represented by Formula 7 (where m is 0, 1, or 2) (Yield: 65%). NMR spectroscopy of the resulting product was:

$^1$H NMR (CDCl$_3$, 300 MHz): δ7.15-6.69(m, 7H), 4.61-3.87 (m, 14H), 1.63-1.17(m, 12H).

SYNTHESIS EXAMPLE 3

Synthesis of 3-methyl-3-(bromomethyl)oxetane (I)

3-methyl-3-(bromomethyl)oxetane was synthesized through Reaction Scheme 3 as follows.

Reaction Scheme 3

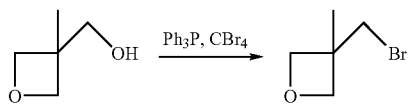

10 ml (0.1 mol) of 3-methyl-3-(hydroxymethyl)oxetane and 36.58 g (0.11 mol) of carbone tetrabromide were dissolved in 100 ml of CH$_2$Cl$_2$. The solution was cooled to 0° C. under nitrogen atmosphere, and 31.56 g (0.12 mol) of triphenylphosphine was gradually added thereto. The mixture was heated to room temperature and stirred for 20 minutes. After the reaction terminated, the solvent was removed under reduced pressure. 100 ml of ethylene acetate was added thereto and the mixture was filtered using celite to remove impurities. After the solvent was removed from the mixture, hexane was added thereto. The mixture was filtered using celite, and concentrated under reduced pressure. The resultant product was fractionally distilled to obtain 16 g of 3-methyl-3-(bromomethyl)oxetane (Yield: 95%). NMR spectroscopy of the resulting product was:

$^1$H NMR (CDCl$_3$, 300 MHz): δ4.46-4.38 (d+d, 4H), 3.65 (s, 2H), 1.44(s, 3H).

SYNTHESIS EXAMPLE 4

Synthesis of 3-methyl-3-(bromomethyl)oxetane (II)

3-methyl-3-(bromomethyl)oxetane was synthesized through Reaction Scheme 4 as follows.

Reaction Scheme 4

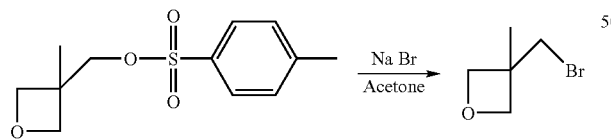

25 g (97.53 mmol) of toluene-4-sulfonic acid 3-methyl-oxetane-3-yl methyl ester synthesized according to Synthesis Example 1 and 50.18 g (0.49 mol) of NaBr were added to 250 ml of acetone, and the mixture was stirred under reflux for 30 hours. The obtained precipitate was filtered, and the mixture was observed until the mixture become colorless by adding charcoal. The charcoal was filtered and the solvent was removed under reduced pressure to obtain 14.8 g of 3-methyl-3-(bromomethyl)oxetane (Yield: 92%). NMR spectroscopy of the resulting product was:

$^1$H NMR (CDCl$_3$, 300 MHz): δ4.46-4.38 (d+d, 4H), 3.65 (s, 2H), 1.44(s, 3H).

SYNTHESIS EXAMPLE 5

Synthesis of oxetane-containing Compound (II)

An oxetane-containing compound was synthesized through Reaction Scheme 5 as follows.

Reaction Scheme 5

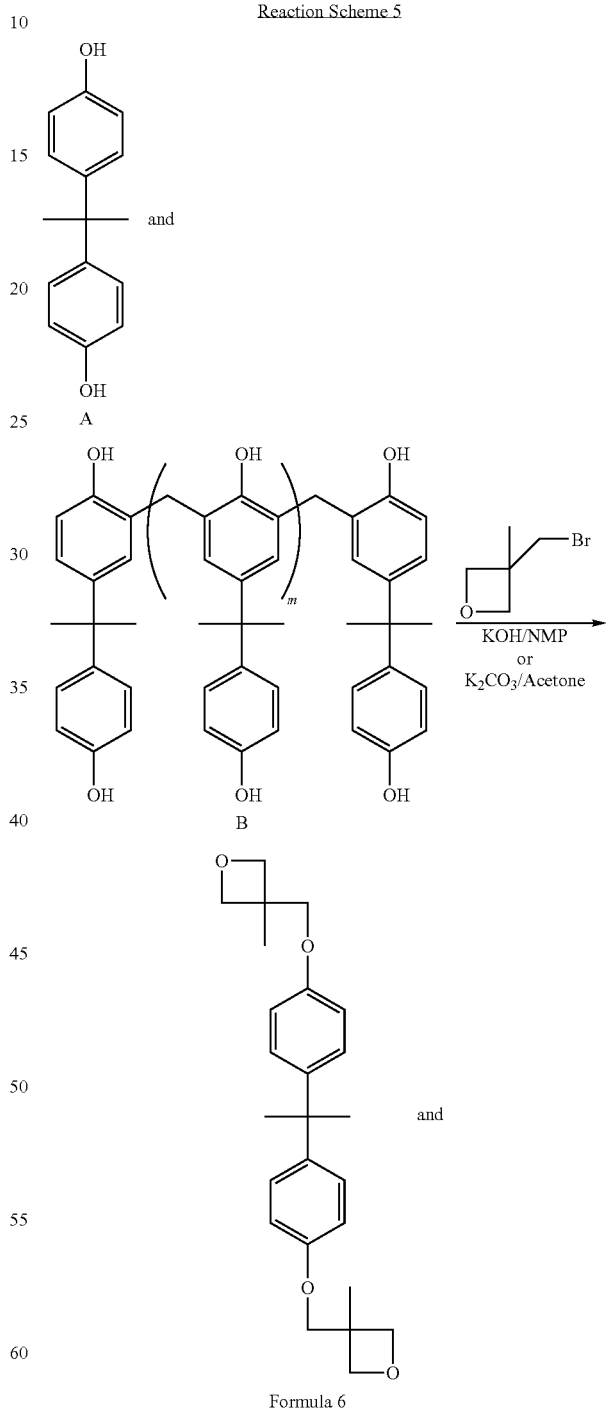

Formula 6

-continued

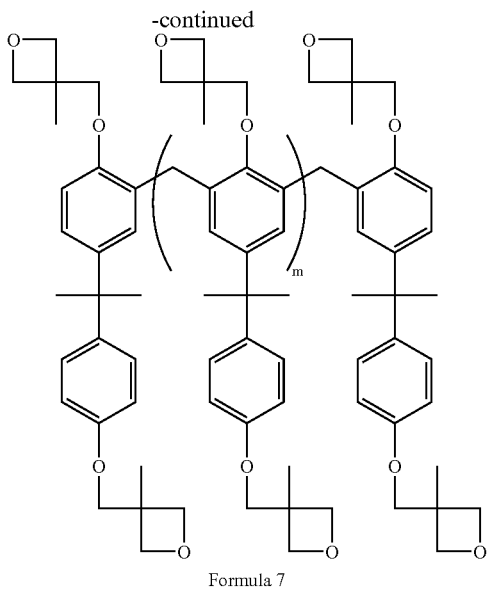

Formula 7

2 g (8.3 mmol) of novolak resin illustrated in Reaction Scheme 5 (a mixture of compound A and compound B illustrated in Reaction Scheme 5, where m is 0, 1 or 2) and 4.1 g (25 mmol) of 3-methyl-3-(bromomethyl)oxetane were dissolved in 100 ml of acetone, and the mixture was refluxed for 2 days. After the reaction terminated, the solvent was removed, 100 ml of $CH_2Cl_2$ was added thereto and the resultant was extracted with water. Water in an organic layer was removed using $MgSO_4$, and the solvent was removed under reduced pressure to obtain 2.3 g of a mixture of a compound represented by Formula 6 and a compound represented by Formula 7 (m is 0, 1 or 2) (Yield: 70%). NMR spectroscopy of the resulting product was:

$^1$H NMR ($CDCl_3$, 300 MHz): δ7.15-6.69(m, 7H), 4.61-3.87 (m, 14H), 1.63-1.17(m, 12H).

Figure 2:
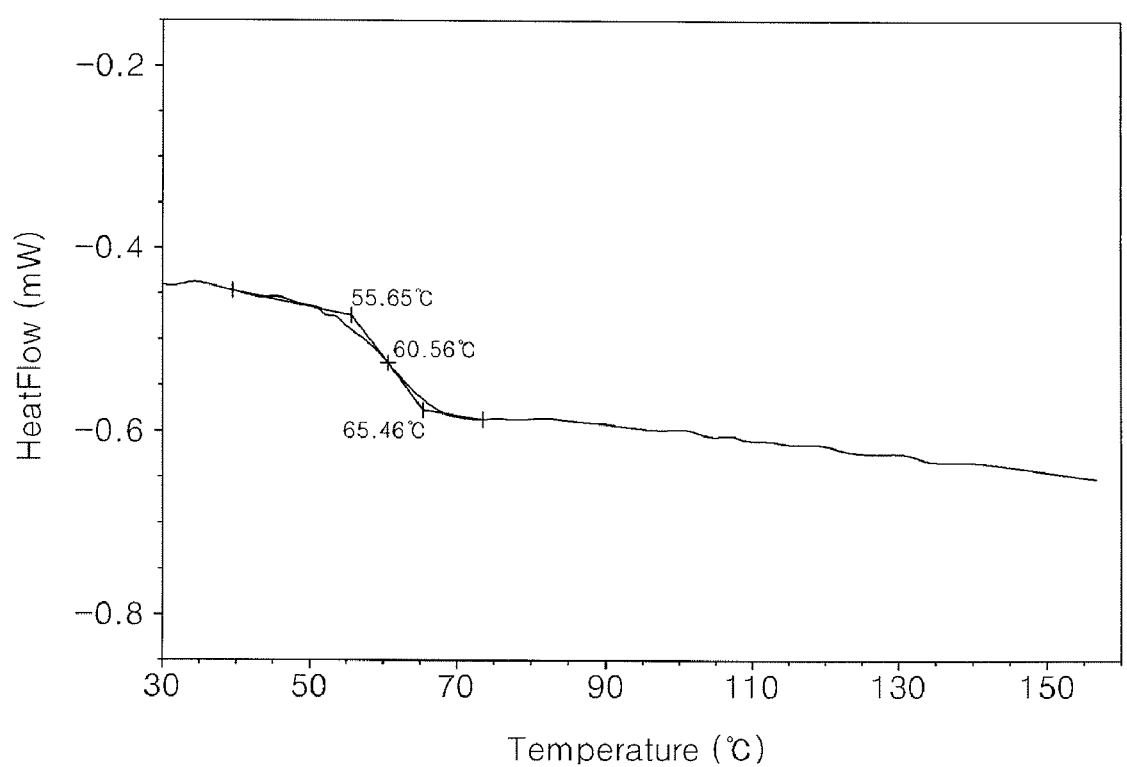
FIG. 2 is a graph illustrating differential scanning calorimetry (DSC) data of an oxetane-containing compound according to an embodiment of the present general inventive concept.

Meanwhile, FIG. 2 is a graph illustrating differential scanning calorimetry (DSC) data of the mixture of the compounds of Formulae 6 and 7. Referring to FIG. 2, Tg of the mixture was about 60° C.

EXAMPLE

Figure 3A:
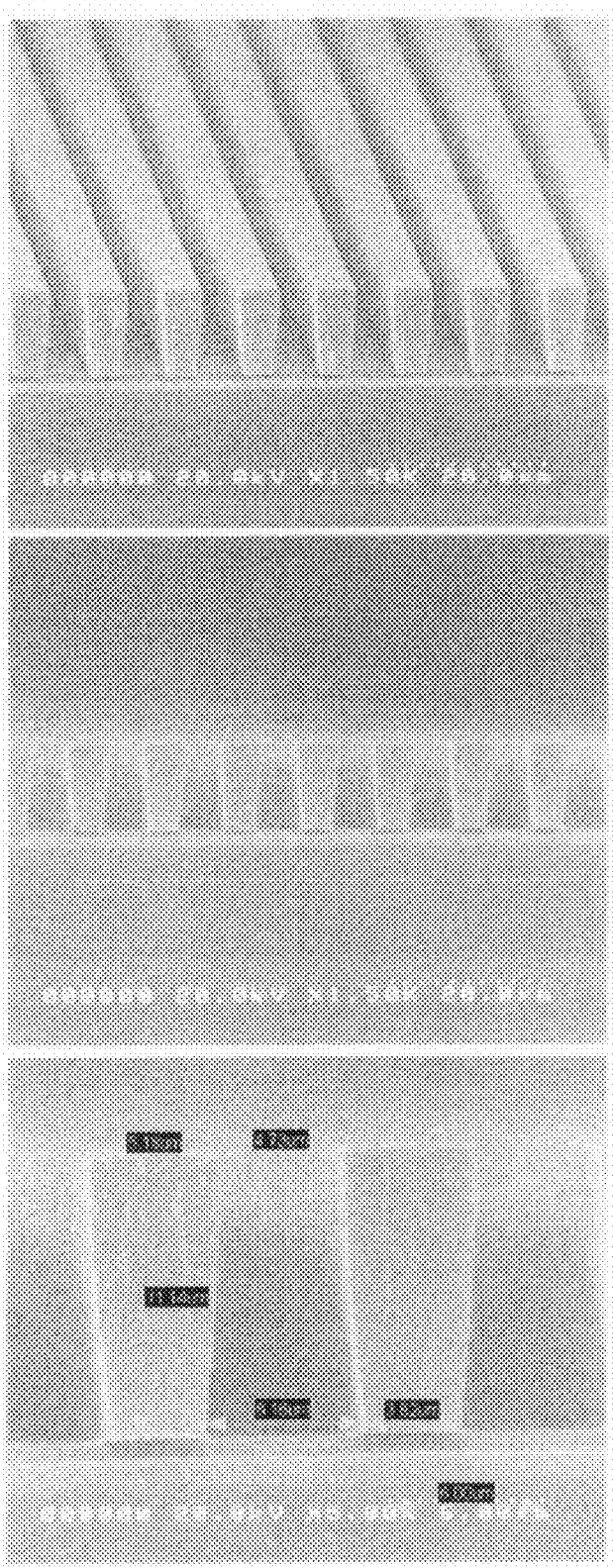
FIGS. 3A and 3B are scanning electron microscopic (SEM) images of a pattern formed by using a photoresist composition according to an embodiment of the present general inventive concept.

Preparation of a Photoresist Composition Including a Mixture of Compounds Represented by Formulae 6 and 7 and Preparation of a Pattern Using the Photoresist Composition 2 g of a mixture of compounds represented by Formulae 6 and 7 obtained according to Synthesis Example 2, 0.3 g of triphenyl sulfonium hexafluoroantimonate (SP-172) obtained from Asahi Denka Co., as a photo initiator, and 0.7 g of gamma-butyrolactone (GBL) as a solvent were mixed and stirred for one day. The mixture was filled with a 5 μm filter to obtain a transparent solution. The transparent solution was spin coated on a silicon substrate at 2000 rpm for 60 seconds, and heated at 65° C. for 3 minutes to obtain a uniform layer. 120 mJ/cm$^2$ I-line was radiated onto the layer using a Hg/Xe lamp exposing device, and heated at 95° C. for 7 minutes. Then, the layer was developed using propylene glycol monomethyl ether acetate (PGMEA) as a developing solution for 1 minute, and washed with PGMEA for 10 seconds to obtain a layer having a stripe type pattern between stripes as illustrated in FIG. 3A (Pattern: 5 μm L/S) and FIG. 3B (Pattern: 10 μm L/S). The obtained layer had excellent thermal resistance, durability, adhesion property, etc.

Figure 3B:
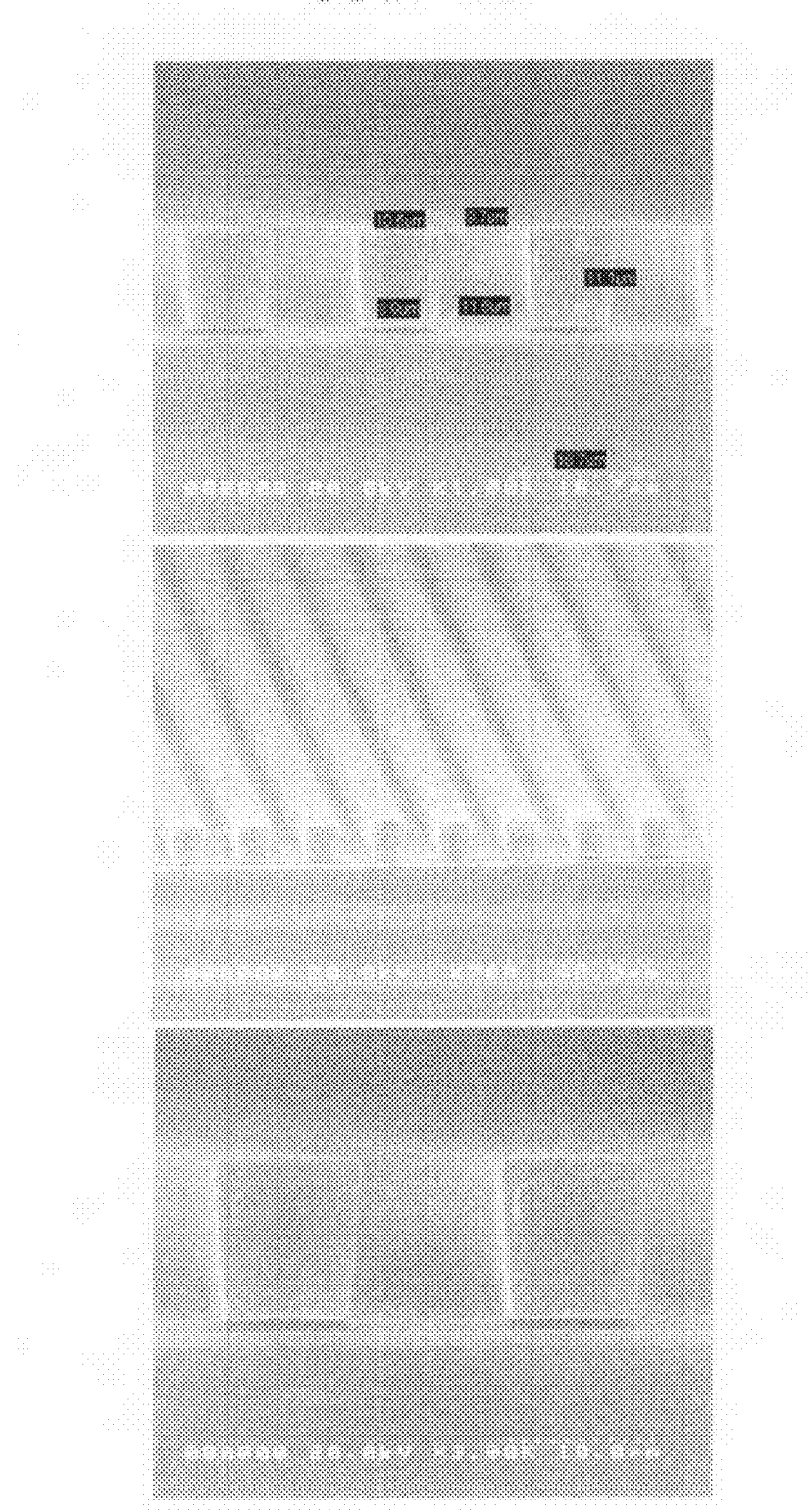
Figure 4:
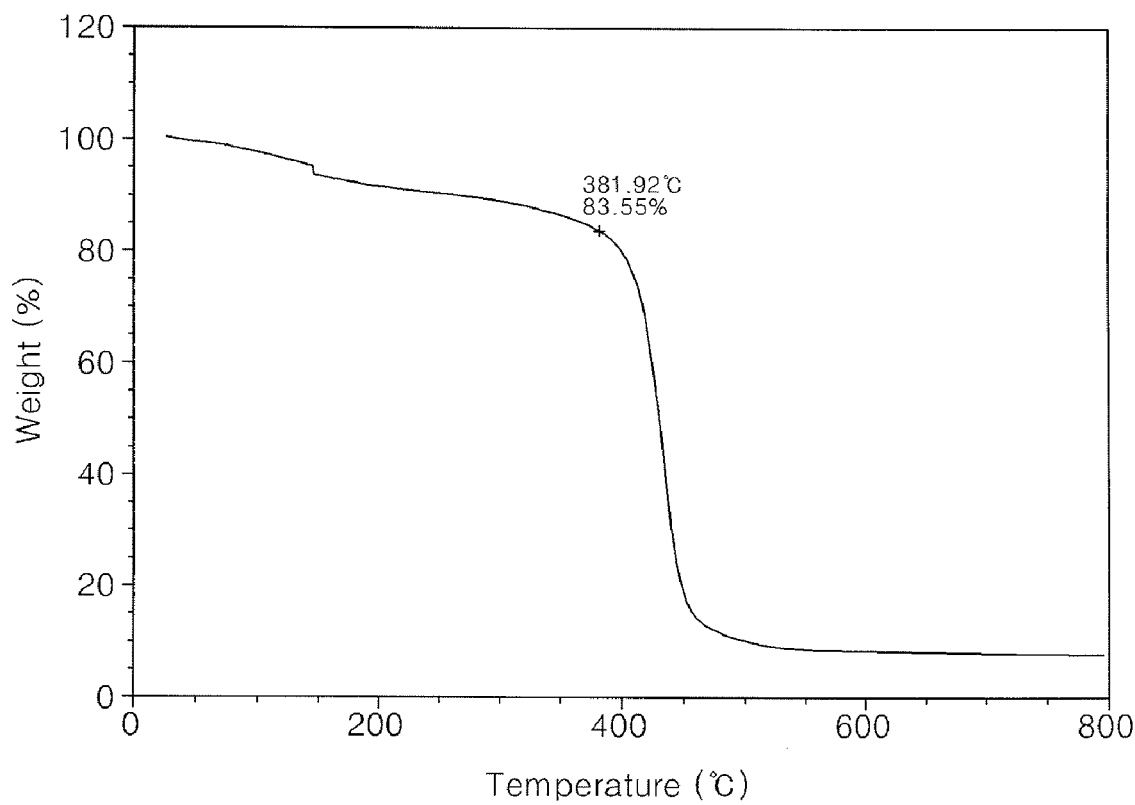
FIG. 4 is a graph illustrating thermogravimetric analysis (TGA) data of a pattern formed using a photoresist composition according to an embodiment of the present general inventive concept.

FIG. 4 is a graph illustrating thermogravimetric analysis (TGA) data of a material forming the layer illustrated in FIGS. 3A and 3B. Referring to FIG. 4, Td of the polymerization product of the oxetane-containing compound according to an embodiment of the present general inventive concept is about 380° C., and thus the oxetane-containing compound has excellent thermal resistance.

Figure 5:
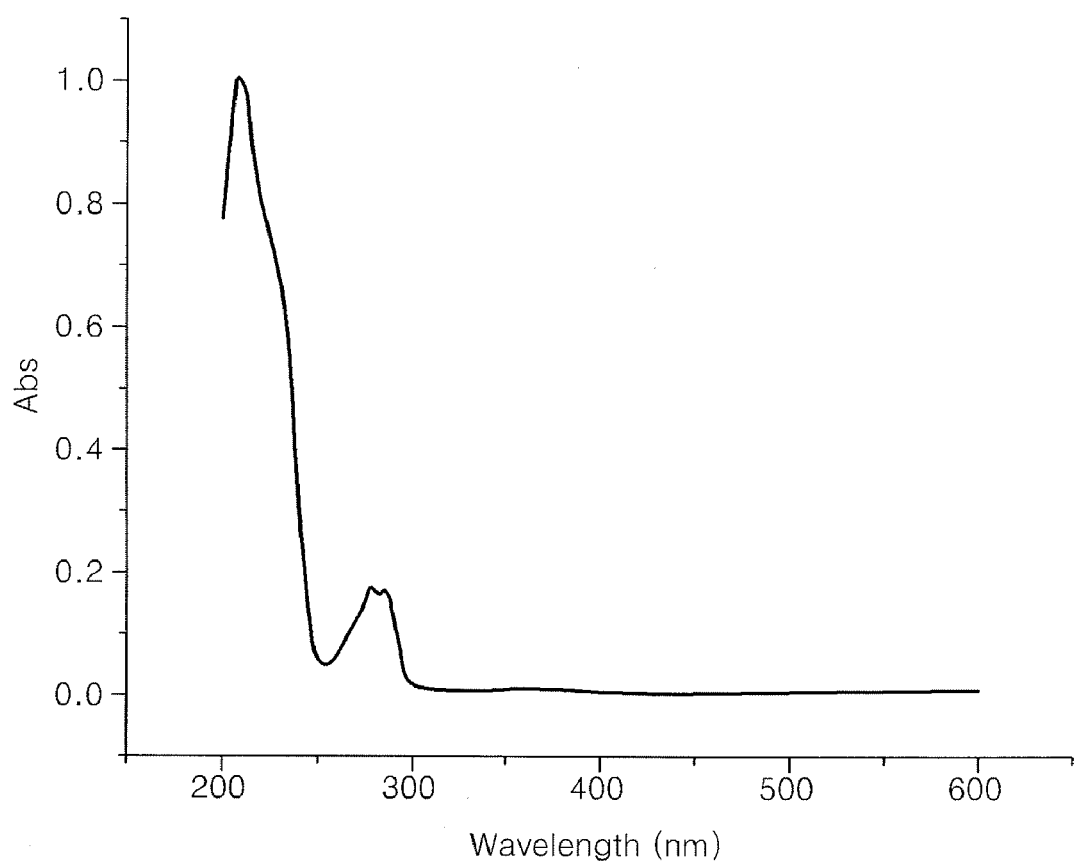
FIG. 5 is a graph illustrating a UV spectrum of a pattern formed using a photoresist composition according to an embodiment of the present general inventive concept.

Meanwhile, a UV spectrum of the layer was measured using a V-530 UV/V is spectrophotometer obtained from Jasco Co., and the results are illustrated in FIG. 5. Referring to FIG. 5, the layer is transparent at 300-400 I-line.

The oxetane-containing compound of the present general inventive concept is an easily polymerizable compound, and thus can be used for a photoresist composition. The polymerization products of the oxetane-containing compound have excellent thermal resistance, chemical resistance, durability, etc., and thus, can be effectively used for various structures, such as a chamber layer and/or a nozzle layer of an inkjet print head, a sacrificial layer of a MEMS switch, and the like.

The oxetane-containing compound is an easily polymerizable and cost effective compound. Further, polymerization products of the oxetane-containing compound have excellent thermal resistance, chemical resistance, adhesion property, durability, etc., and thus the oxetane-containing compound may be effectively used for the photoresist Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

What is claimed is:

1. An oxetane-containing compound represented by Formula 2:

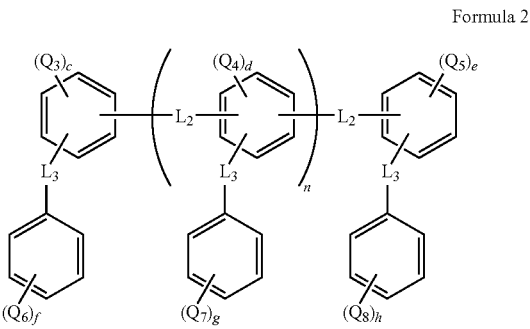

Formula 2 wherein:
$Q_3$, $Q_4$, $Q_5$, $Q_6$, $Q_7$, and $Q_8$ are each independently one of a hydrogen atom, a hydroxyl group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_4$-$C_{30}$ aliphatic hydrocarbon ring, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ acyl group, and a substituted or unsubstituted ether bond-containing monovalent group, $Q_3$, $Q_4$, $Q_5$, $Q_6$, $Q_7$, and $Q_8$ are identical to or different from each other, and at least one of the hydrogen atoms in at least one of $Q_3$, $Q_4$, $Q_5$, $Q_6$, $Q_7$, and $Q_8$ are substituted with an oxetane group, c and e are each independently 1, 2, or 3, d is 1 or 2, f, g, and h are each independently 1, 2, 3, or 4, $L_2$, and $L_3$ are each independently one of a substituted or unsubstituted $C_1$-$C_{30}$ alkylene group, a substituted or unsubstituted $C_2$-$C_{30}$ alkenylene group, a substituted or unsubstituted $C_2$-$C_{30}$ alkynylene group, a substituted or unsubstituted $C_6$-$C_{30}$ arylene group, a substituted or unsubstituted $C_3$-$C_{30}$ heteroarylene group, and a substituted or unsubstituted ether bond-containing divalent group, and n is 0 or an integer 1-10.

2. The oxetane-containing compound of claim 1, wherein the oxetane group is represented by Formula 3:

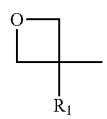

Formula 3 where $R_1$ is one of a hydrogen atom, a halogen atom, a hydroxyl group, a nitro group, a cyano group, an amino group, an amidino group, hydrazine, hydrazone, a carboxyl group and a salt thereof, a sulfonic acid group or a salt thereof, a phosphoric acid or a salt thereof, a carbonyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_6$-$C_{30}$ aryl group, and a substituted or unsubstituted $C_2$-$C_{30}$ heteroadryl group.

3. The oxetane-containing compound of claim 2, wherein $R_1$ is a hydrogen atom or a substituted or unsubstituted $C_1$-$C_{10}$ alkyl group.

4. The oxetane-containing compound of claim 1, wherein $Q_3$, $Q_4$, $Q_5$, $Q_6$, $Q_7$, and $Q_8$ are each independently one of hydrogen atom, a hydroxyl group, a $C_1$-$C_{30}$ alkoxy group substituted with an oxetane group represented by Formula 3 or a carbonyl group, a $C_1$-$C_{30}$ alkyl group substituted with an oxetane group represented by Formula 3 or a carbonyl group, and an ether bond-containing monovalent group substituted with an oxetane group represented by Formula 3 or a hydroxyl group:

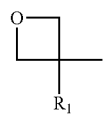

Formula 3 where $R_1$ is one of a hydrogen atom, a halogen atom, a hydroxyl group, a nitro group, a cyano group, an amino group, an amidino group, hydrazine, hydrazone, a carboxyl group and a salt thereof, a sulfonic acid group or a salt thereof, a phosphoric acid or a salt thereof, a carbonyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_6$-$C_{30}$ aryl group, and a substituted or unsubstituted $C_2$-$C_{30}$ heteroaryl group.

5. The oxetane-containing compound of claim 1, wherein $Q_3$, $Q_4$, $Q_5$, $Q_6$, $Q_7$, and $Q_8$ are each independently one of a hydrogen atom and a structure among the structures represented by Formula 4:

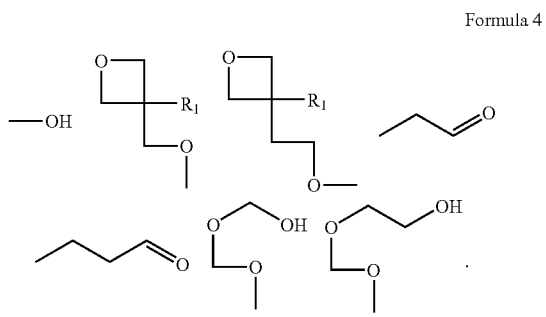

Formula 4

6. The oxetane-containing compound of claim 1, wherein $L_2$, and $L_3$ are each independently at least one structure among the structures represented by Formula 5:

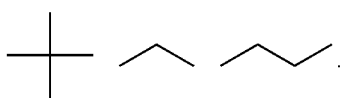

Formula 5

7. The oxetane-containing compound of claim 1, wherein the oxetane-containing compound is represented by Formula 7, and m is 0, 1, or 2:

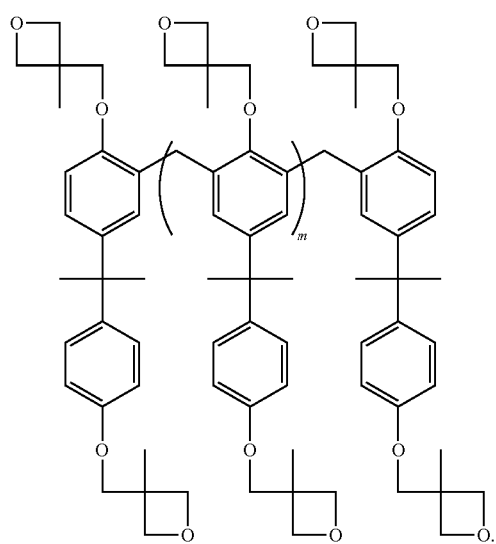

Formula 7

8. A photoresist composition, comprising:

an oxetane-containing compound according to claim 1;

a photo initiator; and a solvent.

9. The photoresist composition of claim 8, wherein the photo initiator is at least one of an onium salt of a Group 15 element, an onium salt of a Group 16 element, and an aromatic halonium salt.

10. The photoresist composition of claim 8, wherein an amount of the photo initiator is in the range of about 5-20 parts by weight based on 100 parts by weight of the oxetane-containing compound.

11. The photoresist composition of claim 8, wherein the solvent is at least one of γ-butyrolactone, cyclopentanone, $C_1$-$C_6$ acetate, tetrahydrofuran, and xylene.

12. The photoresist composition of claim 8, wherein the amount of the solvent is in the range of about 30-100 parts by weight based on 100 parts by weight of the oxetane-containing compound.

13. The photoresist composition of claim 8, further comprising:
   additives,
   wherein the additives are at least one of silane coupling agents, dyestuffs, surfactants, fillers and viscosity modifiers.

14. A method of preparing a pattern, the method comprising:
   coating a photoresist composition having an oxetane-containing compound of claim 8 on a substrate; and
   exposing the coated photoresist composition to light according to a specific pattern and developing the resultant to obtain a structure having the pattern.

15. The method of claim 14, wherein the structure comprises polymerization products of an oxetane-containing compound represented by Formula 2:

Formula 2

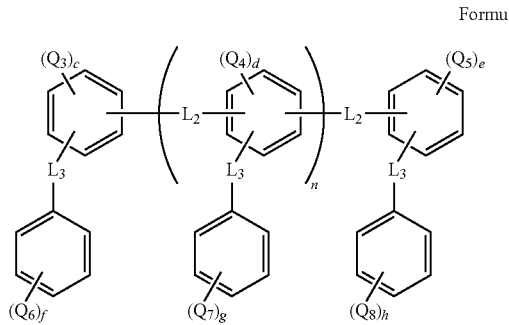

wherein:
$Q_3$, $Q_4$, $Q_5$, $Q_6$, $Q_7$, and $Q_8$ are each independently one of a hydrogen atom, a hydroxyl group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_4$-$C_{30}$ aliphatic hydrocarbon ring, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ acyl group, and a substituted or unsubstituted ether bond-containing monovalent group, $Q_3$, $Q_4$, $Q_5$, $Q_6$, $Q_7$, and $Q_8$ are identical to or different from each other, and at least one of the hydrogen atoms in at least one of $Q_3$, $Q_4$, $Q_5$, $Q_6$, $Q_7$, and $Q_8$ are substituted with an oxetane group, c and e are each independently 1, 2, or 3, d is 1 or 2, f, g, and h are each independently 1, 2, 3, or 4, $L_2$, and $L_3$ are each independently one of a substituted or unsubstituted $C_1$-$C_{30}$ alkylene group, a substituted or unsubstituted $C_2$-$C_{30}$ alkenylene group, a substituted or unsubstituted $C_2$-$C_{30}$ alkynylene group, a substituted or unsubstituted $C_6$-$C_{30}$ arylene group, a substituted or unsubstituted $C_3$-$C_{30}$ heteroarylene group, and a substituted or unsubstituted ether bond-containing divalent group, and n is 0 or an integer 1-10.

16. The method of claim 14, wherein the structure is a chamber layer of an inkjet print head.

17. The method of claim 14, wherein the structure is a nozzle layer of an inkjet print head.

18. The method of claim 14, wherein the structure is a sacrificial layer that is required to manufacture a Micro Electro Mechanical System (MEMS) switch.

19. An inkjet print head comprising:
   a substrate through which an ink feed hole to supply ink is formed;
   a chamber layer comprising a plurality of ink chambers filled with ink supplied from the ink feed hole; and
   a nozzle layer comprising a plurality of nozzles through which the ink is ejected,
   wherein at least one of the chamber layer and the nozzle layer comprises polymerization products of an oxetane-containing compound according to claim 1.

20. The inkjet print head of claim 19, further comprising a plurality of heaters to heat ink in the ink chambers and generate bubbles, and an electrode to apply current to the heaters.

* * * * *